United States Patent [19]

Cartmell et al.

[11] Patent Number: 4,722,761
[45] Date of Patent: Feb. 2, 1988

[54] METHOD OF MAKING A MEDICAL ELECTRODE

[75] Inventors: James V. Cartmell, Dayton; Michael L. Wolf, West Milton, both of Ohio

[73] Assignee: Baxter Travenol Laboratories, Inc., Dayton, Ohio

[21] Appl. No.: 845,600

[22] Filed: Mar. 28, 1986

[51] Int. Cl.$^4$ .............................................. B32B 31/12
[52] U.S. Cl. ................................ 156/242; 128/303.13; 128/640; 128/798
[58] Field of Search ............ 156/242, 252, 253, 307.1, 156/307.3, 307.7; 128/303.13, 640, 798

[56] References Cited

U.S. PATENT DOCUMENTS

| | | | |
|---|---|---|---|
| 3,601,126 | 8/1971 | Estes | 128/303.14 |
| 3,848,600 | 11/1974 | Patrick, Jr. et al. | 128/303.13 |
| 4,303,073 | 12/1981 | Archibald | 128/303.13 |
| 4,365,634 | 12/1982 | Bare et al. | 128/798 |
| 4,367,745 | 1/1983 | Welage | 128/303.13 |
| 4,539,996 | 9/1985 | Engel | 128/798 |
| 4,554,924 | 11/1985 | Engel | 128/798 |

Primary Examiner—Caleb Weston
Attorney, Agent, or Firm—Killworth, Gottman, Hagan & Schaeff

[57] ABSTRACT

A method of making an electrosurgical patient electrode includes the steps of initially providing an electrode body having a recess defined therein with an electrically conductive bottom surface, and then casting a quantity of uncured hydrogel material into the recess. The gel material is sufficient in volume to fill the recess and is subsequently cured in situ.

16 Claims, 5 Drawing Figures

METHOD OF MAKING A MEDICAL ELECTRODE

BACKGROUND OF THE INVENTION

The present invention relates to a method of making a medical electrode and, more particularly, to a method of making a disposable electrosurgical patient electrode which includes a layer of cured, electrically conductive hydrogel material.

In various types of medical procedures, it is necessary to establish good electrical contact with the skin of a patient. During electrosurgical procedures, for example, an electrosurgical generator produces a high frequency electric current which is supplied an active electrode. The active electrode is used by the surgeon to cut tissue, and to coagulate blood vessels, and the like. To provide a return path for the electrosurgical current to the generator, an indifferent, or patient, electrode is placed in contact with the skin of the patient and connected by a lead to the return terminal of the generator. By maintaining a large area in contact with the electrode, the current density is held to a sufficiently low level to avoid damage to the skin at the indifferent electrode attachment site.

Various types of electrodes have been utilized in the past. Disposable, single-use electrodes have become increasingly popular for electrosurgical procedures. Such electrodes are shown, for example, in U.S. Pat. No. 3,848,600, issued Nov. 19, 1974, to Patrick et al and U.S. Pat. No. 3,601,126, issued Aug. 24, 1971, to Estes. The Patrick et al patent discloses an indifferent electrode which includes a sponge pad which is soaked with an electrode jelly material. Similarly, the Estes patent discloses a porour sheet of spongy material which is soaked with a viscous saline solution. Although providing good electrical contact with a patient's skin, disposable electrodes, carrying a pad soaked with an electrolyte paste, are somewhat messy and require that the application site be subsequently cleaned. Additionally, some types of electrolyte paste may tend to dry out if improperly stored, resulting in a loss in conductivity.

Medical electrodes for use as diagnostic electrodes and as surgical electrodes have been developed using various hydrogel materials. Such a hydrogel material is a three dimensional network of hydrophillic polymer material, which is generally covalently or ionically cross-linked and which contains a high level of water. Hydrogel materials are advantageous in that they can be made to be tacky, providing good adhesion to and electrical contact with, a patient's skin, while at the same time being sufficiently cohesive such that a residue of hydrogel material is not left on the skin of a patient when the electrode is removed and discarded. Due to the nature of such hydrogel materials, however, they have previously been difficult to handle in the electrode manufacturing process.

Accordingly, there is a need for an improved method of making a medical electrode for providing electrical contact with the skin of patient, which includes a quantity of cured hydrogel material.

SUMMARY OF THE INVENTION

The above need is met by a method according to the present invention for making an electrosurgical patient electrode, which includes the steps of providing a flexible support layer of electrically non-conductive material, and mounting a layer of flexible, electrically conductive material on the support layer to produce a flexible backing layer having an electrically conductive surface on one side thereof. The method further includes the step of mounting a flexible, apertured layer of electrically non-conductive material on the one side of the flexible backing layer. The apertured layer defines an aperture through which at least a portion of the electrically conductive surface is exposed, thereby producing a recess having an electrically conductive bottom surface. The method further includes the steps of pouring a quantity of uncured, substantially fluid, electrically conductive hydrogel material into the recess so as to fill the recess, and then curing the hydrogel material.

The step of providing a flexible support layer of electrically non-conductive material may include the step of providing a flexible layer of electrically non-conductive foam material. The foam material may be a polyethylene foam.

The step of mounting a layer of flexible, electrically conductive material on the support layer may include the step of mounting a layer of flexible, electrically conductive foil material on the support layer. Alternatively, the step of mounting a layer of flexible, electrically conductive material on the support layer may include the step of mounting a layer of plastic having a metal coating on the support layer with the metal coating exposed. The layer of plastic may be a polyester layer having an aluminum coating thereon.

The flexible apertured layer may be approximately 100 mils in thickness so as to define a recess approximately 100 mils in depth.

The layer of flexible, electrically conductive material may define a connection tab. The step of mounting a layer of flexible, electrically conductive material may comprise the step of mounting the layer with the connection tab extending laterally from the backing layer, whereby electrical connection may be made to the tab. The method may further include the step of attaching a relatively thin layer of electrically non-conductive material over a portion of the tab to facilitate making electrical connection to the tab while preventing direct contact between the skin of a patient and the tab.

The layer of flexible, electrically conductive material may be adhesively mounted on the support layer and the flexible, apertured layer may be adhesively mounted on the flexible backing layer.

Accordingly, it is an object of the present invention to provide a method of making a disposable medical electrode of the type including a quantity of cured, electrically conductive, hydrogel material, in which the material is cast onto an electrically conductive support surface in an uncured state and subsequently cured; to provide such a method in which the electrically conductive surface is defined by the bottom of a recess, said recess holding the uncured hydrogel material prior to curing; to provide such a method in which an apertured layer is mounted on a backing layer to define the recess; and to provide such a method in which the hydrogel material is cured in situ.

Other objects and advantages of the invention will be apparent from the following description, the accompanying drawings and the appended claims.

DETAILED DESCRIPTION OF THE PREFERRED EMBODIMENT

Figure 1:
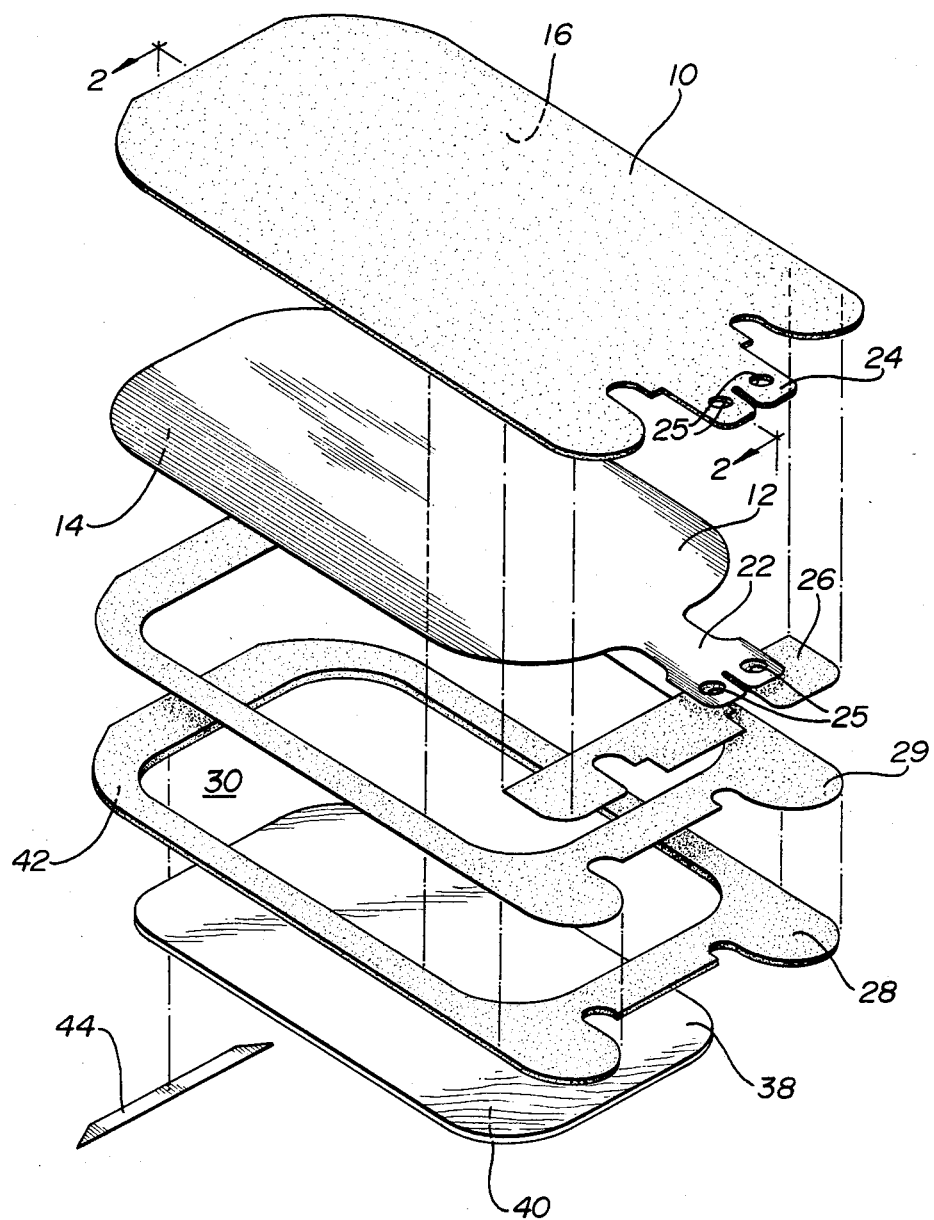
FIG. 1 is an exploded perspective view of a disposable electrosurgical electrode of the type produced by the method of the present invention.
Figure 2:
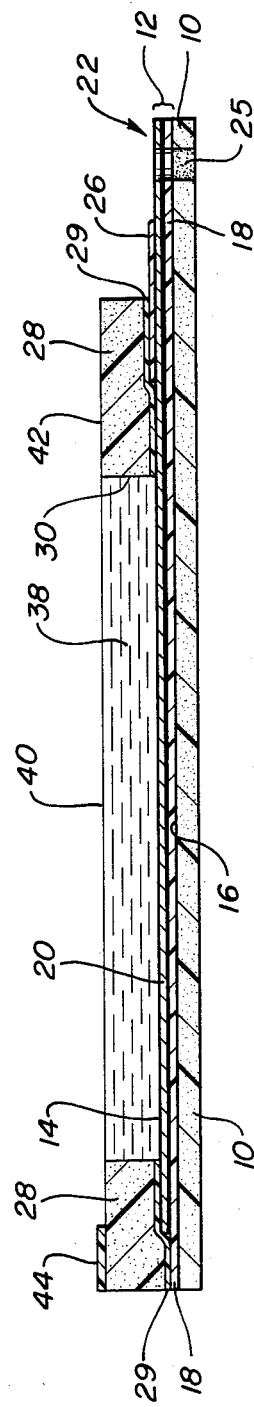
FIG. 2 is a sectional view taken generally along line 2—2 in FIG. 1.

Reference is made to FIGS. 1 and 2 which illustrate a disposable, electrosurgical patient electrode of the type which may be made according to the present invention. The patient electrode is shown in FIG. 1 facing downward, that is oriented for application to the skin of a patient beneath the electrode, whereas FIG. 2 depicts the electrode facing upward. As may be noted, the electrode is made up of a number of different layers of material.

A flexible support layer 10 of an electrically non-conductive material and a layer 12 of flexible, electrically conductive material, mounted on the support layer 10, together consititute a flexible backing layer having an electrically conductive surface 14 on one side thereof. The flexible support layer 10 may be a polyethylene foam layer which is secured to layer 12 on upper surface 16 by an adhesive therebetween, as seen in FIG. 2. The layer 12 of flexible, electrically conductive material may consist of a layer of plastic 18 having a metal coating 20 thereon. Layer 18 may be a layer of polyester material coated with a thin layer 20 of aluminum. Alternatively, layer 12 may comprise a layer of metal foil, such as an aluminum foil.

The flexible, electrically conductive layer 12 may define a connection tab 22 for attachment to an electrical connector securing one or more electrical leads to the tab 22 so as to provide an electrical path from the surface 14 through the leads to the electrosurgical generator. As shown in FIG. 1, the support layer 10 may also include a tab portion 24. Holes 25 extend through layers 10 and 12 for securing a connector to the tab.

A relatively thin layer 26 of electrically nonconductive material, such as an adhesive coated Mylar tape, may be mounted across a portion of the tab 22 and the support layer 10 so as to cover a portion of the tab. Layer 26 thereby prevents this portion of tab 22 from making direct contact with the skin of a patient to which the electrode is applied.

Figure 3:
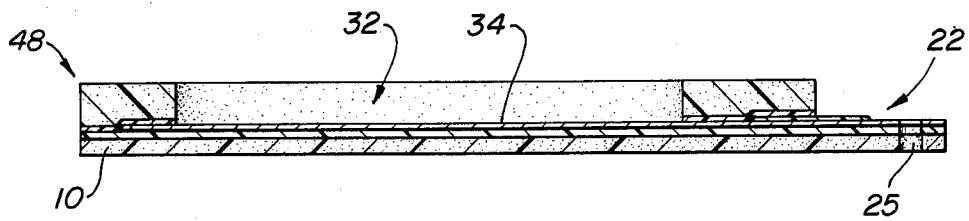
FIGS. 3, 4, and 5 are sectional views, similar to FIG. 2, illustrating the steps by which the electrode is made.

A flexible, apertured layer 28 of electrically non-conductive material is mounted on the flexible backing layer by means of an apertured layer 29 of thin non-conductive material carrying adhesive on both sides thereof. The apertured layer 28 defines an aperture 30 through which at least a portion of the electrically conductive surface 14 is exposed. As best seen in FIG. 3, the backing layer and the apertured layer 28 thereby define a recess 32 having an electrically conductive bottom surface 34. The apertured layer 28 may preferably comprise a polyethylene foam layer which is approximately 100 mils in thickness so as to define a recess 32 approximately 100 mils in depth. Layer 28 is secured to surface 16 of the flexible support layer 10 and to portions of the flexible electrically conductive layer 12 which it may overlie by the adhesive coated apertured layer 29. Layer 12, if desired, may be no larger than aperture 30 and centrally locating within aperture 30, such that layer 29 is not attached to layer 12. It will be appreciated that it is desirable that the conductive coating 14 not extend to the edges of the layer 10, in any event. Coating 20 need not be coextensive with layer 18 if, for example, layer 18 is generally the same size as layer 10.

Positioned within the recess 32 is a quantity of a cured, electrically conductive, hydrogel material 38. Material 38 may be any one of a number of known gel materials which provide a tacky surface 40 for good electrical contact with the skin of a patient. A pressure-sensitive adhesive coating may be provided on upper surface 42 of the apertured layer 28, as seen in FIG. 2, so as to hold the electrode in position on the patient's skin. As a consequence, an electrical path is provided by the electrode from the surface 40 of the material 38 to the electrically conductive layer 12, such that the electrosurgical current may be returned to the electrosurgical generator through a lead wire or wires attached to tab 22 by an appropriate connector.

A tab 44 may be mounted across an end of the apertured layer 28. Tab 44, which may consist of a relatively thin strip of electrically non-conductive polyester film, covers a portion of the adhesive on surface 42. When a sheet of release material 46 (FIG. 5) is positioned to cover the hydrogel material 40 prior to use of the electrode, one end of the release sheet layer 46 may therefore be easily raised. This facilitates the stripping away of layer 46 to reveal the hydrogel material 38 prior to the application of the electrode to the skin of a patient.

Figure 4:
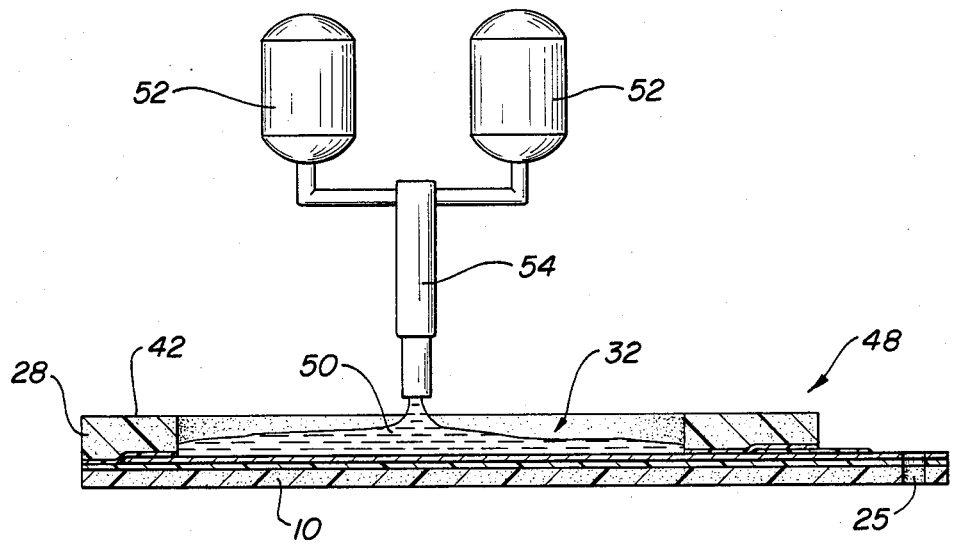
Figure 5:
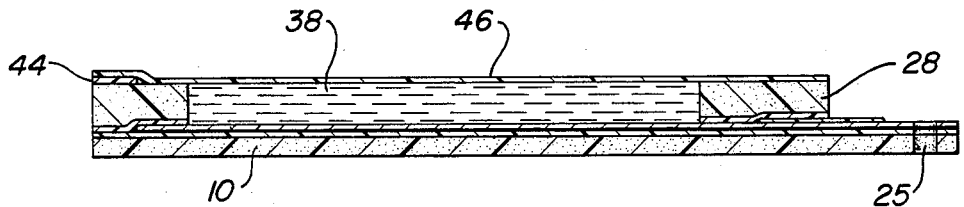

The method according to the present invention for making an electrosurgical patient electrode is illustrated in FIGS. 3–5. As shown in FIG. 3, an electrode body 48 is provided having a recess 32 defined therein with an electrically conductive bottom surface 34. As noted previously, surface 34 is electrically connected to tab 22.

The electrode body 48 may be assembled by adhesively attaching the various layers 10, 12, 26, 38, and 28. All of the layers may have been cut previously into the shapes illustrated in FIG. 1. Alternatively, some of the layers making up the electrode body 48 may be cut in subsequent operations, after assembly.

After the body 48 is assembled to define the recess 32, the recess is filled by pouring or casting a quantity of uncured hydrogel material 50 therein. The hydrogel material 50 may be a mixture of a number of components stored in separate tanks 52 and mixed in conventional static mixing apparatus 54 just prior to being supplied to recess 32. Since the hydrogel material is at this point uncured, it flows sufficiently to form a level surface 40 adjacent the top surface 42 of the body 48. Next, the hydrogel material 50 is cured, resulting in the cured hydrogel material 38 being appropriately positioned in the electrode to function in the manner described above. Depending upon the type of hydrogel material utilized, curing can be effected in a number of ways, for example through the action of a catalyst or by exposure to microwave radiation.

Advantageously, a release sheet 46 may then be placed over the hydrogel material 38, and held in position by the adhesive on surface 42. Tab 44 may be added at this time. Alternatively, tab 44 may have been added prior to filling the recess 32 with the uncured hydrogel material.

It will be appreciated that by curing the material 38 in situ in the electrode body, handling of the tacky, cured hydrogel material is eliminated, and manufacture of the medical electrode is thereby facilitated.

Having described the invention in detail and by reference to the preferred embodiment thereof, it will be apparent that modifications and variations are possible without departing from the scope of the invention defined in the appended claims.

What is claimed is:

1. A method of making an electrosurgical patient electrode, comprising the steps of:
   providing a flexible support layer of electrically non-conductive material,
   mounting a layer of flexible, electrically conductive material on said support layer to produce a flexible backing layer having an electrically conductive surface on one side thereof,
   mounting a flexible, apertured layer of electrically non-conductive material on said one side of said flexible backing layer, said apertured layer defining an aperture through which at least a portion of said electrically conductive surface is exposed, said backing layer and said apertured layer thereby defining a recess having an electrically conductive bottom surface,
   pouring a quantity of uncured, substantially fluid, electrically conductive, hydrogel material into said recess so as to fill said recess, and
   curing said gel material.

2. The method of claim 1 in which said step of providing a flexible support layer of electrically non-conductive material includes the step of providing a flexible layer of electrically non-conductive foam material.

3. The method of claim 2 in which said foam material is a polyethylene foam material.

4. The method of claim 1 in which said step of mounting a layer of flexible, electrically conductive material on said support layer includes the step of mounting a layer of flexible, electrically conductive foil material on said support layer.

5. The method of claim 1 in which said step of mounting a layer of flexible, electrically conductive material on said support layer includes the step of mounting a layer of plastic, having a metal coating, on said support layer with said metal coating exposed.

6. The method of claim 5 in which said layer of plastic is a polyester layer having an aluminum coating thereon.

7. The method of claim 1 in which said flexible apertured layer is approximately 100 mils in thickness so as to define a recess approximately 100 mils in depth.

8. The method of claim 1 in which said layer of flexible, electrically conductive material defines a connection tab, and in which the step of mounting a layer of flexible, electrically conductive material comprises the step of mounting said layer with said connection tab extending laterally from said backing layer, whereby electrical connection may be made to said tab.

9. The method of claim 8 further comprising the step of attaching a relatively thin layer of electrically non-conductive material over a portion of the tab to facilitate making electrical connection to said tab while preventing direct contact between the skin of a patient and said tab.

10. The method of claim 1 in which said layer of flexible, electrically conductive material is adhesively mounted on said support layer, and in which said flexible, apertured layer is adhesively mounted on said flexible backing layer.

11. A method of making a medical electrode including a cured gel material for providing electrical contact with the skin of a patient, comprising the steps of:
    providing a flexible backing layer having an electrically conductive surface on at least a portion of one side thereof,
    mounting a flexible, electrically non-conductive layer on said one side of said backing layer, said non-conductive layer defining an opening such that at least a portion of said conductive surface is exposed through said opening, and a recess, having an electrically conductive bottom surface, is defined,
    pouring a quantity of an uncured, electrically conductive gel material into said recess, and
    curing said gel material.

12. The method of claim 11 in which said uncured gel material fills said recess and conforms to the shape of said recess.

13. The method of claim 11 further comprising the step of covering said recess with a sheet of release material.

14. The method of claim 11 in which said electrically non-conductive layer and said backing layer are adhesively bonded together.

15. A method of making a disposable electrode of the type which includes a quantity of electrically conductive, cured gel material for contacting the skin of a patient, comprising:
    providing an electrode body having a recess defined therein with an electrically conductive bottom surface, said bottom surface being in direct electrical communication with a connection tab extending from said electrode body,
    casting a quantity of uncured hydrogel material into said recess, said hydrogel material being sufficient in volume to fill said recess, and
    curing said hydrogel material.

16. The method of claim 15 in which said electrode body carries a layer of pressure sensitive adhesvie thereon, surrounding said recess, and further including the step of placing a layer of release material over said recess, secured to said pressure sensitive adhesive.

* * * * *